(12) United States Patent
Lu et al.

(10) Patent No.: US 6,387,980 B2
(45) Date of Patent: May 14, 2002

(54) DENTAL COMPOSITION SYSTEM AND METHOD

(75) Inventors: Kewang Lu, Dover; Paul D. Hammesfahr, Wyoming, both of DE (US)

(73) Assignee: Dentsply Research & Development Corp.

(*) Notice: Subject to any disclaimer, the term of this patent is extended or adjusted under 35 U.S.C. 154(b) by 0 days.

(21) Appl. No.: 09/725,430

(22) Filed: Nov. 29, 2000

Related U.S. Application Data

(62) Division of application No. 09/351,231, filed on Jul. 12, 1999, now Pat. No. 6,211,264, which is a division of application No. 08/742,019, filed on Nov. 1, 1996, now Pat. No. 5,973,022.

(51) Int. Cl.[7] .............................. A61K 6/083; C08J 3/28
(52) U.S. Cl. .................. 523/116; 523/115; 523/118; 433/228.1; 522/26; 522/28; 522/60; 522/18; 522/64; 524/450; 524/791
(58) Field of Search ................................ 523/109, 115, 523/116, 117, 118; 433/228.1; 522/13, 20, 18, 60, 64; 524/450, 791

(56) References Cited

U.S. PATENT DOCUMENTS

| | | | |
|---|---|---|---|
| 3,709,866 A | 1/1973 | Waller | 323/115 |
| 3,825,518 A | 7/1974 | Foster et al. | 523/116 |
| 4,222,780 A | 9/1980 | Shibatani et al. | 106/35 |
| 4,235,633 A | 11/1980 | Tomioka et al. | 106/35 |
| 4,259,117 A | 3/1981 | Yamauchi et al. | 106/35 |
| 4,265,723 A | 5/1981 | Hesse et al. | 204/159.23 |
| 4,368,043 A | 1/1983 | Yamauchi et al. | 433/217 |
| 4,459,193 A | 7/1984 | Ratcliffe et al. | 523/116 |
| 4,499,251 A | 2/1985 | Omura et al. | 526/278 |
| 4,514,342 A | 4/1985 | Billington et al. | 433/228.1 |
| 4,553,940 A | 11/1985 | Koblitz et al. | 523/115 |
| 4,657,941 A | 4/1987 | Blackwell et al. | 522/14 |
| 4,668,712 A | 5/1987 | Hino et al. | 522/13 |
| 4,674,980 A | 6/1987 | Ibsen et al. | 523/116 |
| 4,918,136 A | 4/1990 | Kawaguchi et al. | 523/116 |
| 4,920,188 A | 4/1990 | Sakashita et al. | 526/196 |
| 5,151,479 A | 9/1992 | Mukai et al. | 526/277 |
| 5,154,762 A | 10/1992 | Mitra et al. | 106/35 |
| 5,204,383 A | 4/1993 | Manabe et al. | 523/118 |
| 5,270,351 A | 12/1993 | Bowen | 523/115 |
| 5,334,625 A * | 8/1994 | Ibsen et al. | 523/115 |
| 5,338,773 A | 8/1994 | Lu et al. | 523/116 |
| 5,367,002 A | 11/1994 | Huang et al. | 523/116 |
| 5,472,991 A | 12/1995 | Schmitt et al. | 522/4 |
| 5,554,030 A | 9/1996 | Ario et al. | 433/226 |
| 5,645,429 A | 7/1997 | Blackwell et al. | 523/115 |

FOREIGN PATENT DOCUMENTS

| | | |
|---|---|---|
| EP | 0325266 | 7/1989 |
| EP | 0554890 | 8/1993 |
| JP | 61223069 A | 10/1986 |
| WO | WO 97 29732 | 8/1997 |

* cited by examiner

*Primary Examiner*—Peter Szekely
(74) *Attorney, Agent, or Firm*—Dale R. Lovercheck; James B. Bieber

(57) ABSTRACT

The invention provides dental composition system having curable liquid which is useful alone as a light curable composition and which is useful by mixing with a powder in preselected proportions to form dual cure compositions. The composition system is useful as bonding agent, cement, liner, base, restorative, pit and fissure sealants, and/or core build-up material, having improved adhesion to dentin. After storing the powder and the liquid in separate containers for at least two weeks and then mixing a portion of the powder and a portion of the liquid to form a mixture, the polymerizable compound polymerizes within 20 minutes of the mixing to form a first polymeric material having a flexural strength of at least 50 MPa, and an expansion in water at 37° C. after 90 days of less than 1 percent by volume.

20 Claims, No Drawings

DENTAL COMPOSITION SYSTEM AND METHOD

This application is a division of application Ser. No. 09/351,231 filed Jul. 12, 1999 now U.S. Pat. No. 6,211,264 which is a division of application Ser. No. 08/742,019, filed Nov. 1, 1996 now U.S. Pat. No. 5,973,022.

The invention relates to dental compositions. In particular the invention provides dental composition system which polymerizes in-situ by reaction between polymerizable monomers and/or prepolymers. Dental composition systems in accordance with the invention are useful as dental cement, liner, base, restorative, core build-up material and pit and fissure sealants. A liquid composition is useful alone as a sealant. The liquid is also useful by mixing the liquid in preselected proportions with a powder containing glass.

It is the object of the invention to provide a method of using a dental composition system having a liquid composition and a powder composition. The liquid composition is enclosed by a first container and includes a polymerizable compound, a photoinitiator, and a first part of a redox polymerization catalyst system. The powder composition is enclosed by a second container and includes filler powder and a second part of the polymerization redox catalyst system. A first tooth surface is cleaned and then a first portion of the liquid is applied to the first tooth surface. A second portion of the liquid is mixed with a first portion of the powder to form a first mixture, which is applied to a second tooth surface.

Huang et al in U.S. Pat. No. 5,367,002 disclose a light curable dental composition and method which includes a powder in combination with a liquid. Lu et al in U.S. Pat. No. 5,338,773 disclose dental composition and method which includes a powder in combination with a liquid. The prior art does not disclose a dual cure dental composition and method which includes a powder in combination with a liquid, which after storing the powder and liquid in separate containers for at least two weeks, polymerizes within 20 minutes of mixing the powder and liquid to form a polymeric material having a flexural strength of at least 50 MPa as is provided by the invention.

The invention overcomes the problems of the prior art.

Excavating carie dentin as used herein refers to the removal of dentin softened by decay by a hand held tool which does not have a motor.

Peroxide decay and peroxide decomposing as used herein refer to break down of peroxide compounds which initiate or facilitate polymerization to compounds which do not initiate or facilitate polymerization.

BRIEF DESCRIPTION OF THE INVENTION

The invention provides dental composition system having curable liquid which is useful alone as a light curable composition and which is useful by mixing with a powder in preselected proportions to form dual cure compositions. The composition system is useful as cement, liner, base, restorative, pit and fissure sealants, and/or core build-up material, having improved adhesion to dentin. A dual cure dental composition includes a powder in combination with a liquid, which includes polymerizable compounds. After storing the powder and liquid in separate containers for at least two weeks, the polymerizable compounds polymerize within 20 minutes of mixing the powder and liquid to form a first polymeric material having a flexural strength of at least 50 MPa, and an expansion in water at 37° C. after 90 days of less than 1 percent by volume. More preferably the polymerizable compounds polymerize within 10 minutes of mixing the powder and liquid to form a polymeric material having a flexural strength of at least 50 MPa. The liquid is stored in a container for at least two weeks and a portion of the liquid is exposed to actinic light and polymerizes within 40 seconds to form a second polymeric material having an expansion in water at 37° C. after 90 days of less than 1 percent by volume. More preferably the polymerizable compounds polymerize within 10 minutes of exposing the liquid to liquid to form a polymeric material having a flexural strength of at least 50 MPa, and an expansion in water at 37° C. after 90 days of less than 1 percent by volume.

A storage stable polymerizable liquid composition which includes a polymerizable phosphoric acid compound and a peroxide compound. Preferably, while in the liquid composition, the peroxide compound decomposes within one week at 23° C. by less than or about equal to the percent of decomposition of tert-Butyl peroxybenzoate (TBPO) within one week at 23° C. The liquid polymerizes within 40 seconds from the moment of exposing the liquid to light (exposure to light is typically for about 2–10 seconds) to form a polymeric material having an expansion of less than 1 percent by volume after 90 days in water at 37° C.

DETAILED DESCRIPTION OF THE INVENTION

In a preferred embodiment, the invention provides a curable liquid useful alone and useful with a powder in preselected proportions to form dental cement, liner, base, restorative, pit and fissure sealants, and core build-up material. For mixtures, the ratio preferably used is from 0.5 to 6 parts by weight powder to 1 part by weight liquid. The liquid is cured by exposure to visible light. The liquid and powder mixtures self cure.

A preferred embodiment of the invention provides a method of using a dental composition system having a liquid composition and a powder composition. The liquid composition is enclosed by a first container and includes a polymerizable compound, a photoinitiator, and a first part of a redox polymerization catalyst system. The powder composition is enclosed by a second container and includes filler powder and a second part of the polymerization redox catalyst system. A first tooth surface is cleaned and then a first portion of the liquid is applied to the first tooth surface. A second portion of the liquid is mixed with a first portion of the powder to form a first mixture, which is applied to a second tooth surface. Preferably the first tooth surface is exposed to light whereby the liquid composition is cured on the first tooth surface.

In a preferred embodiment of the invention, the first tooth surface is in a first patient's mouth and the second tooth surface is in a second patient's mouth. The second tooth surface is preferably treated for example by etching the second tooth enamel surface, by excavating carie dentin or by drilling into the dentin thereof. Preferably the second portion of the liquid and the first portion of the powder are mixed in a weight ratio of between 1 to 5 and 4 to 1. More preferably the second portion of the liquid and the first portion of the powder are mixed in a weight ratio of between 1 to 3.4 and 1 to 4.5.

In a preferred embodiment of the invention a bracket is applied to the second tooth. Preferably a third portion of the liquid is mixed with a second portion of the powder to form a second mixture, which is applied the second mixture to a third tooth surface. Preferably, the powder includes fluoride elutable glass.

The compositions of the invention preferably contain powder elute fluoride ion to reduce the solubility of adjacent enamel and dentin and reduce the incidence of secondary caries.

Compositions of the present invention which include powder may be light cured to provide filling materials especially useful in Class III and Class V restorations. They are also useful as core build-up materials at high filler solids concentrations with good strength values and insensitivity to trace interfacial water, the combination of which is an improvement in this invention.

The liquid alone is useful as a light curable dental sealant. The liquid mixed with the powder is useful to provide consistencies suitable for use as dual cure pit and fissure sealants. Mixtures of the liquid and powder in ratios of powder to liquid of from about 3.5 to 1 to about 5 to 1 are useful as dual cure restoratives and as bases of low solubility and good strength under other filling materials including conventional composites and amalgams. The powder containing compositions polymerize rapidly and preferably elute fluoride ions which can react with hydroxyapatite of the tooth to form the less acid-soluble fluorapatite structure to reduce the risk of caries adjacent the filling.

In accordance with an embodiment of the invention, intermediate solids concentrations having ratios of powder to liquid of from about 1.2 to 1 to about 1.8 to 1 are provided for dual curing adhesive dental cements used under light-transmitting glass-ceramic inlays, crowns, dental veneers, orthodontic, brackets, or to fill pits and fissures in teeth according to current dental practice.

Dual cure compositions of the invention utilize two catalyst systems to cause them to harden promptly. Thus for example, for light curing the catalyst system includes 1) a light sensitizer, for example (2,4,6-trimethyl benzoyl) phosphine oxide, causes polymerization to be initiated upon exposure to activating wavelengths of light; and 2) a reducing compound. Accelerators for the polymerization, for example metal salts such as copper acetyl-acetonate, phosphinic acids and phosphinates, may also be used. A room temperature activating catalyst system comprised of a redox polymerization system is employed advantageously with the compositions of the invention by adding, for example, a peroxide capable of producing free radicals when activated by a reducing agent at such temperature. Peroxides useful in the invention include tert-Butyl peroxybenzoate (TBPO). Suitable promoters include the same reducing agents and accelerators used in light curing catalyst systems. Preferably dual curable dental compositions of the invention are comprised of 0.01 to 10 parts by weight, more preferably 0.02 to 5 parts by weight, and most preferably 0.03 to 4 parts by weight, of a two catalyst system ingredients in the polymerizable powder and liquid composition.

Preferably dual curable dental compositions of the invention include 1 to 60 percent by weight, more preferably 2 to 50 percent by weight, most preferably 2 to 40 percent by weight, of an acid functional polymerizable organic compound in the cured composition. In accordance with a preferred embodiment of the invention, liquids contain polymerizable acid functional materials having ethylenic unsaturation include, among others, organic esters of one or more acids of phosphorus (hereinafter referred to as phosphorus acid esters), wherein the organic portion of the ester contains at least one polymerizable ethylenically unsaturated group. The organic portion of the ester may be alkenyl, alkenoxy, cycloalkenyl, aralkenyl, or alkenaryl, and preferably may have from 2 to 40 carbon atoms. The organic portion may be straight chain, branches, or cyclic, can contain skeletal hetero atoms, i.e., atoms other than carbon, and can be unsubstituted or substituted with moieties which do not interfere with the free radical polymerization of the phosphorus acid esters. Examples of unsaturated phosphorus containing acid esters which may be used include, but are not limited to, monomers containing phosphoric acid groups such as hydroxyethyl methacrylate monophosphate, 2,2,-bis($\alpha$-meth-acryloxy-$\beta$-hydroxy-propoxyphenyl)propane diphosphonate (BIS-GMA diphosphonate), BIS-GMA diphosphate, methacryloxyethyl phosphate, and glyceryl dimethacrylate phosphate. Other suitable polymerizable acid esters are disclosed, for example, in U.S. Pat. No. 4,499,251 to Omura et al, U.S. Pat. No. 4,222,780 to Shibantani et al, U.S. Pat. No. 4,235,633 to Tomioka, U.S. Pat. No. 4,259,117 to Yamauchi et al, U.S. Pat. No. 4,368,043 to Yamauchi et al, and Sakashita in U.S. Pat. No. 4,920,188.

In accordance with a preferred embodiment of this invention, the liquid contains polymerizable phosphate acid ester monomers which are reactive with cations eluted from the reactive fillers. Upon polymerization, alone or in combination with other polymerizable components, these form polyacids which are also reactive with cations. Polymerizable phosphates preferred for use with this invention are adhesive to tooth structure and improve the adhesion of the compositions.

In accordance with an embodiment of the invention the liquid composition preferably includes phosphoric acid esters:

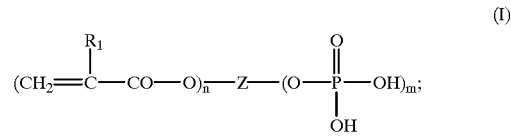

(I)

wherein $R_1$ is hydrogen, lower alkyl of from 1 to 5 carbons, halogen or CN radical; n and m are independently integers of 1 or greater, Z is an aliphatic, cycloaliphatic or aryl radical having a carbon chain comprising at least 2 carbon atoms and 0 or more oxygen or sulfur atoms and having a valency of m+n. In a preferred embodiment of the invention, the phosphoric acid esters used are those compositions of Formula I wherein m is 1.

In accordance with a further embodiment of the invention, acid esters within the scope of Formula I are partially neutralized to form phosphoric acid esters of the general Formula II and III as follows:

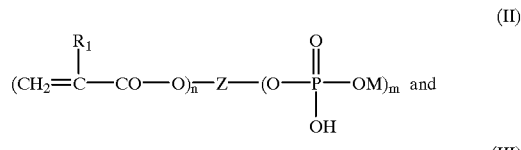

(II)

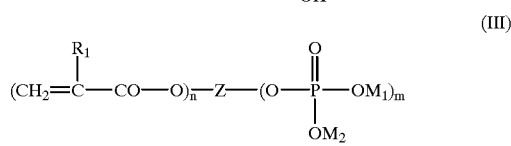

(III)

wherein M, $M_1$ and $M_2$ each is independently a cation, such as K, Li, Na, $NH_4$ or an amine. Preferably 20–40 equivalent weight percent of the phosphoric acid ester is neutralized by reaction with base.

Preferably the polymerizable liquid composition includes a polymerizable carboxylic acid compound, such as 4,4'-oxydiphenylether-1,1,6,6"-tetracarboxylic acid 1,1'-(methacryloxy)dimethacrylate (OEMA) to adhere the polymeric material formed to metal containing substrates for example brackets and crowns. Preferably the photoinitiator is a phosphine oxide.

Liquid compositions of the invention preferably include polymerizable unsaturated substituted aromatic compounds containing at least one acid moiety. These aromatic compounds are preferably within the scope of the general formula (I):

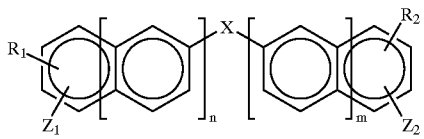

wherein

X, is O, S,

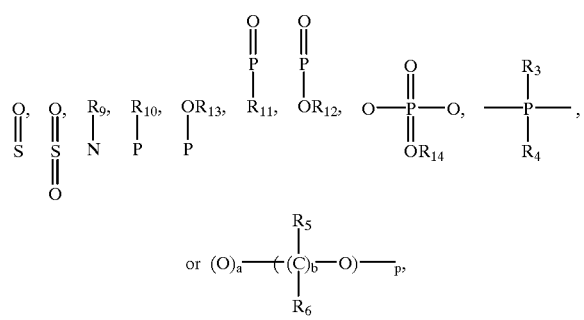

wherein $R_1$ and $R_2$ each independently is a polymerizable unsaturated moiety having from 2 to 13 carbon atoms, $R_3$, $R_4$, $R_5$, and $R_6$ each independently is hydrogen, halogen, alkyl having from 1 to 10 carbon atoms or halogenated alkyl of from 1 to 10 carbon atoms, $R_9$, $R_{10}$, $R_{11}$, $R_{12}$, $R_{13}$ and $R_{14}$ each independently is hydrogen, alkyl having from 1 to 10 carbon atoms or aryl having from 6 to 10 carbon atoms.

$Z_1$ and $Z_2$ each independently is a moiety including an acid group or a reactive acid derivative, a ,m and n each independently is 0 or 1, b and p each independently is an integer from 1 to 10.

In accordance with a preferred embodiment of the invention $R_1$ and $R_2$ each independently is:

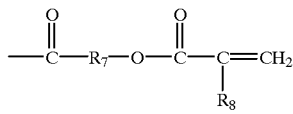

wherein $R_7$ a divalent carbon containing radical and $R_8$ is hydrogen, halogen or alkyl having from 1 to 10 carbon atoms.

In a preferred embodiment of the invention compounds are provided within the scope of general formula I wherein n and m are zero, X is oxygen, sulfonyl or ditrifluoromethyl; $Z_1$ and $Z_2$ are —COO(M) wherein M is hydrogen or an alkali metal, alkaline-earth metal, amine or amine salt; and $R_1$ and $R_2$ are

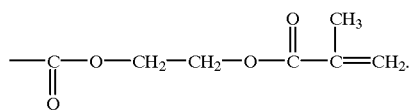

Most preferably compounds within the scope of general formula I are those wherein X is oxygen, and M is hydrogen, Li, Na or K. Appropriate polymerizable unsaturated groups $R_1$ and $R_2$ independently are alkenyl, alkenoxy, cycloalkenyl, arylalkenyl, and alkenaryl moieties; with vinyl, and styryl moieties being preferred, and acryl and methacryl moieties that constitute the polymerizable groups of many monomers in dental materials being especially preferred.

In accordance with an embodiment of the composite composition, phosphoric acid esters useful in the composition include:

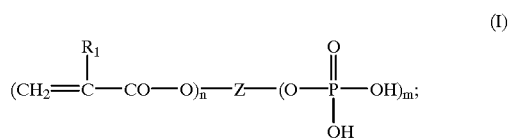

wherein $R_1$ is hydrogen, lower alkyl of from 1 to 5 carbons, halogen or CN radical; n and m are independently integers of 1 or greater, Z is an aliphatic, cycloaliphatic or aryl radical having a carbon chain comprising at least 2 carbon atoms and 0 or more oxygen or sulfur atoms and having a valency of m+n. In a preferred embodiment of the invention, the phosphoric acid esters used are those compositions of Formula I wherein m is 1.

Polymerizable liquid compositions include monomers and/or prepolymers selected to form, in combination with the other ingredients of the liquid composition of the invention, a balance of properties in the liquid prior to polymerization, as well as in the polymerized product. These include mutual solubility, stability, viscosity, mechanical strength and physical integrity of the cured materials, biotolerance, and the like. Monomers useful as polymerizable monomer in accordance with the invention include those disclosed in Dentsply's U.S. Pat. Nos. 3,825,518, 3,709,866, 4,553,940, 4,514,342, and 4,657,941. Including ethylene glycol dimethacrylate, triethylene glycol dimethacrylate, dipropylene glycol dimethacrylate, BIS-GMA, 1,1,6 trimethyl hexamethylene urethane dimethacrylate, cyclohexyl methacrylate, hydroxyethyl methacrylate, glycerol mono-, di- and trimethacrylates. Prepolymers useful in accordance with the invention include adducts formed by the reaction of BIS-GMA and 1,1,6 trimethyl hexamethylene diisocyanate, the adducts formed between polyethers and diisocyanates end capped with hydroxyethyl methacrylate, the adducts formed by polyethers or polyalcohols with an isocyanato methacrylate such as isocyanatoethyl methacrylate. By substituting the methacrylate function of these monomers and prepolymers with the corresponding acrylate, fluoroacrylate, or cyanoacrylate function, additional, polymerizable moieties are provided for use as monomers or prepolymers in accordance with the invention. Preferably curable dental compositions of the invention include 1 to 60 parts by weight, more preferably 2 to 50 percent by weight, most preferably 5 to 40 percent by weight, of polymerizable monomer and/or prepolymer in the cured composition.

Preferred reactive fillers for use in accordance with the invention preferably include elutable cations having a valence of 2 or more, for example, strontium, calcium, zinc, aluminum, iron, zirconium. Elutable glasses also preferably contain elutable fluoride ion, for example, finely ground aluminosilicate and silicate glasses including, for example without limitation, calcium fluoroaluminosilicate glasses, strontium fluoroalumino-silicates, strontium-calcium fluoroaluminosilicates and the like. Preferably curable dental powder compositions of the invention include 10 to 90 percent by weight, more preferably 20 to 90 percent by weight, most preferably 30 to 90 percent by weight, reactive glass in the cured composition.

As used herein, non-reactive fillers are characterized as those which do not form hardened coherent products within 10 hours by reaction between the glass filler and a 50% aqueous solution of the polyacid after being mixed at a ratio of 2 g powder to 1 gram polyacid solution. Non-reactive fillers are optionally included in compositions of the invention to include beneficial properties. For example, fumed silica is a non-reactive filler which is included to provide viscosity control, and barium alumino-silicate is a non-reactive filler included to extend the composition, and increase its strength and radiopacity. Curable dental compositions in accordance with one embodiment of the invention include preferably 1 to 60 percent by weight, more preferably 4 to 40 percent by weight, most preferably 4 to 30 percent by weight, of the non-reactive filler in the cured composition.

In accordance with a preferred embodiment of the invention is provided a storage stable polymerizable liquid composition which includes a polymerizable phosphoric acid compound and a peroxide compound which decomposes by less than 50 percent within one week at 23° C. A preferred peroxide is TBPO. Such compositions are stable for at least 2 weeks and more preferably at least one month and less preferably at least 6 months. Such liquid compositions in accordance with the invention preferably polymerize within 20 minutes and more preferably within 10 minutes of exposure to actinic light.

Preferably, both reactive and non-reactive fillers are included having a coating such as an organic phosphate for compatibility with the organic components of the compositions. A suitable organic phosphate is pentaerythritol trimethacrylate phosphate. Alternative coatings, especially for the non-reactive fillers, include organic silane, such as gamma methacryloxy propyl trimethoxy silane applied by procedures well known in the art.

Preferably, compositions in accordance with the invention are water tolerant to reduce the effects of surface contamination by water which may affect adhesion between tooth and restorative. Preferably, compositions in accordance with the invention more nearly match the coefficient of thermal expansion than do conventional composites to permit greater longevity to the adhesive bond formed. Preferably, compositions in accordance with the invention are radiopaque through the use of an radiopaque non-reactive fillers.

EXAMPLE 1

Powder for use with liquids in accordance with the invention is formed by adding 96.83 parts by weight strontium aluminofluorosilicate glass; 1.0 parts by weight benzoyl peroxide; 0.15 parts by weight ascorbyl palmitate FCC concentrate, 0.02 parts by weight cupric acetylacetonate and 2.0 parts by weight sodium fluoride.

EXAMPLE 2

Powder for use with liquids in accordance with the invention is formed by adding 95.66 parts by weight strontium aluminofluorosilicate glass; 2.0 parts by weight benzoyl peroxide; 0.3 parts by weight ascorbyl palmitate FCC concentrate, 0.04 parts by weight cupric acetylacetonate and 2.0 parts by weight sodium fluoride.

EXAMPLE 3

Polymerizable liquid prepared by mixing 17.0 parts by weight of 4,4'-oxydiphenylether-1,1,6,6"-tetracarboxylic acid 1,1'-(methacryloxy)dimethacrylate (OEMA), 1.0 parts by weight of water, 42.6 parts by weight of bisphenol-A glycidyl dimethacrylate (Bis GMA); 28.4 parts by weight triethyleneglycol dimethacrylate; 10.0 parts by weight dipentaerythritol pentacrylate phosphoric acid ester (PENTA); 0.5 parts by weight of tert-Butyl peroxybenzoate (TBPO) and 0.5 parts by weight diphenyl (2,4,6-trimethyl benzoyl)phosphine oxide (L-TPO).

EXAMPLE 4

Polymerizable liquid prepared by mixing 17.0 parts by weight of 4,4'-oxydiphenylether-1,1,6,6"-tetracarboxylic acid 1,1'-(methacryloxy)dimethacrylate (OEMA), 1.0 parts by weight of water, 40 parts by weight of bisphenol-A glycidyl dimethacrylate (Bis GMA); 30.5 parts by weight triethyleneglycol dimethacrylate; 10.0 parts by weight dipentaerythritol pentacrylate phosphoric acid ester (PENTA); 1.0 parts by weight of tert-Butyl peroxybenzoate (TBPO) and 0.5 parts by weight diphenyl (2,4,6-trimethyl benzoyl)phosphine oxide (L-TPO).

EXAMPLE 4A

The polymerizable liquid prepared in Example 4 is brushed onto a cleaned tooth and then exposed to light to from a sealant coating on the tooth.

EXAMPLE 4B

The polymerizable liquid prepared in Example 3 is brushed onto a cleaned tooth and then exposed to light to from a sealant coating on the tooth.

EXAMPLE 5

A mixture suitable as a dental cement is prepared by mixing 2.5 parts by weight of the powder formed as in Example 2 with 1 part by weight of the polymerizable liquid formed as in Example 4. Samples are applied to a tooth surface in a patient's mouth and self polymerizes within 10 minutes to form a cured polymeric material.

EXAMPLE 6

A mixture suitable as a dental liner is prepared by mixing 2.5 parts by weight of the powder formed as in Example 2 with 1 part by weight of the polymerizable liquid formed as in Example 4. Samples are applied to a tooth surface in a patient's mouth and polymerized by exposing to actinic light using a Caulk MAX curing light.

EXAMPLE 7

A mixture suitable as a dental base is prepared by mixing 5.0 parts by weight of the powder formed as in Example 2 with 1 part by weight of the polymerizable liquid formed as in Example 4. Samples are applied to a tooth surface in a patient's mouth and polymerized by exposing to actinic light using a Caulk MAX curing light.

EXAMPLE 8

A mixture useful as a dental restorative is prepared by mixing 5.0 parts by weight of the powder formed as in Example 2 with 1 part by weight of the polymerizable liquid of Example 4. The mixture is applied to a tooth surface in a human patient's mouth and self polymerizes.

EXAMPLE 9

A mixture useful as a dental restorative is prepared by mixing 5.0 parts by weight of the powder formed as in Example 1 with 1 part by weight of the polymerizable liquid of Example 3. The mixture is applied to a tooth surface in a human patient's mouth and self polymerizes.

EXAMPLE 10

A mixture useful as a dental restorative is prepared by mixing 5.0 parts by weight of the powder formed as in Example 1 with 1 part by weight of the polymerizable liquid of Example 3. The mixture is applied to a tooth surface in a human patient's mouth, and is polymerized using light to form a cured polymeric material.

The ratios of powder and liquid used in Examples 4A and 5 through 8 are shown in Table 1.

TABLE 1

| Example | CEMENT 5 | LINER 6 | BASE 7 | RESTOR-ATIVE/ CORE BUILD-UP 8 | SEALANT 4A |
|---|---|---|---|---|---|
| POWDER/ LIQUID RATIO | 2.5/1 | 2.5/1 | 5.0/1 | 5.0/1 | |
| LIQUID | | | | | 100% |

Example C1

This is a comparative example and corresponds exactly with Example 5 of U.S. Pat. No. 5,367,002 (Case 1627).

Example C2

This is a comparative example and corresponds exactly with Example 15A of U.S. Pat. No. 5,338,773.

The polymerizable composition of Examples 4A and C1 are light cured to form polymeric material having the physical properties shown in TABLE 2. The polymerizable compositions of Examples 8, 9 and C2 are self cured to form polymeric material having the physical properties shown in TABLE 2. Flexural strength (MPa) is measured by ISO 4049. Bond strength to dentin (psi) is measured by the Huang method of Example 4 (column 9, lines 61–68 through column 10, lines 1–22) in U.S. Pat. No. 5,367,002. Linear expansion (percent) is measured after 7 days in water at 37° C.

TABLE 2

| Example | 4A | 9 | 8 | C1 | C2 |
|---|---|---|---|---|---|
| Flexural Strength (MPa) | 61 | 71 | 70 | 31 | 31 |
| Bond Strength to Dentin (psi) | 1695 | 839 | 1631 | 1097 | 1522 |
| Compressive Strength (MPa) | 335 | 175 | 206 | 184 | 149 |
| Linear expansion in water at 37° C. after 7 days (percent) | 0.9 | 0.16 | — | 1.7 | 1.5 |

TABLE 2-continued

| Example | 4A | 9 | 8 | C1 | C2 |
|---|---|---|---|---|---|
| Linear expansion in water at 37° C. after 90 days (percent) | — | 0.5 | — | — | 3.3 |
| Cure Depth at 2 months at 50° C. (mm) | more than 15 | N. A. | N. A. | 0 | N. A. |

*In Table 2 N. A. means Not Applicable

Preferably the liquid composition includes a polymerizable compounding having a carboxylic acid containing moiety. An example of a preferred compound is OEMA.

Preferably mixtures of powder and liquid form polymerizable material which polymerizes an adheres to dentin with an adhesion of at least 700 psi and adheres to metal containing substrates such as crowns and brackets with an adhesion of at least 500 psi.

Various alteration and modifications of this invention will be apparent to those skilled in the art without departing from the scope and spirit of this invention, and it should be understood that this invention is not limited to the illustrative embodiments set forth herein.

What is claimed is:

1. A dental composition system, comprising:
    a liquid composition in a first container and a powder composition in a second container,
    said liquid composition comprising a polymerizable compound, a photoinitiator, and a first part of a redox polymerization catalyst system,
    said powder composition comprising filler powder and a second part of said redox polymerization catalyst system,
    said powder being stored in said second container and said liquid being stored in said first container for at least two weeks and a first portion of said powder being mixed with a first portion of said liquid to form a first polymerizable mixture, said polymerizable compound in said first polymerizable mixture polymerizing within 20 minutes of said mixing to form a first polymeric material having a flexural strength of at least 50 MPa,
    a second portion of said liquid being exposed to actinic light and polymerizing within 40 seconds of said exposing to form a second polymeric material having an expansion in water at 37° C. after 7 days of less than 1 percent by volume.

2. A dental method, comprising:
    providing a liquid composition in a first container and a powder composition in a second container,
    said liquid composition comprising a polymerizable compound, a photoinitiator, and a first part of a redox polymerization catalyst system,
    said powder composition comprising filler powder and a second part of said redox polymerization catalyst system,
    storing said powder in said second container,
    storing said liquid in said first container for at least two weeks and
    mixing a first portion of said powder with a first portion of said liquid to form a first polymerizable mixture,
    exposing said first polymerizable mixture to actinic light, said polymerizable compound in said first polymerizable mixture polymerizing within 20 minutes of said mixing to form a first polymeric material having a flexural strength of at least 50 MPa, exposing a second portion of said liquid to actinic light and polymerizing said second portion of said liquid within 40 seconds of said exposing to form a second polymeric material having an expansion in water at 37° C. after 7 days of less than 1 percent by volume.

3. The composition of claim 1 wherein said liquid further comprises an ethylenically unsaturated organic phosphate ester or phosphonate.

4. The composition of claim 1 wherein said liquid further comprises ethylenically unsaturated organic phosphoric acid ester and said acid ester is from about 20 to about 40 equivalent weight percent neutralized.

5. The composition of claim 1 wherein said first polymeric material has an expansion in water at 37° C. after 90 days of less than 1 percent by volume, and said powder comprises glass having elutable strontium ions.

6. The composition according to claim 1 wherein said second polymeric material has a flexural strength of at least 50 MPa.

7. The composition of claim 1 wherein said liquid further comprising an acid ester is of the general formula:

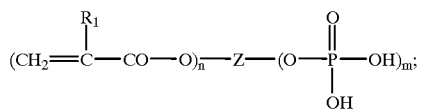

wherein $R_1$ is hydrogen, lower alkyl of from 1 to 5 carbons, halogen or CN radical; n and m are independently integers of 1 or greater, Z is an aliphatic, cycloaliphatic or aryl radical, having a carbon chain comprising at least 2 carbon atoms and 0 or more oxygen or sulfur atoms and having a valency of m+n and containing at least 2 carbon atoms.

8. The composition of claim 1 wherein said liquid further comprises an acid ester mixture of compounds of the general formulas:

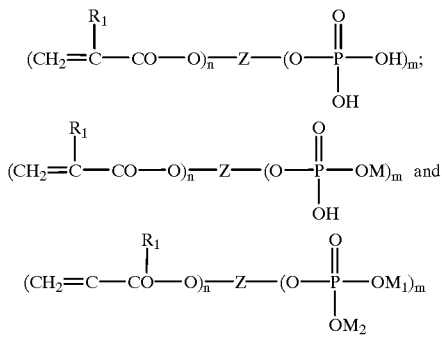

wherein $R_1$ is hydrogen, lower alkyl of from 1 to 5 carbons, halogen or CN radical; n and m are independently integers of 1 or greater, Z is an aliphatic, cycloaliphatic or aryl radical having a carbon chain comprising at least 2 carbon atoms and 0 or more oxygen or sulfur atoms and having a valency of m+n and M, $M_1$ and $M_2$ each is independently a cation.

9. The composition of claim 1 wherein said filler comprises from about 20 to 90 percent by weight of said composition.

10. The composition of claim 1 wherein said photoinitiator is a phosphine oxide.

11. The composition of claim 1 wherein said photoinitiator is 2,4,6-trimethyl benzoyl phosphine oxide.

12. A dental composition system, comprising:
a liquid composition in a first container and a powder composition in a second container,
said liquid composition comprising a polymerizable compound, a phosphine oxide photoinitiator, and a first part of a redox polymerization catalyst system,
said powder composition comprising filler powder and a second part of said redox polymerization catalyst system,
said powder being stored in said second container and said liquid being stored in said first container for at least two weeks and a first portion of said powder being mixed with a first portion of said liquid to form a first polymerizable mixture, said polymerizable compound in said first polymerizable mixture polymerizing within 20 minutes of said mixing to form a first polymeric material having a flexural strength of at least 50 MPa,
a second portion of said liquid being exposed to actinic light and polymerizing within 40 seconds of said exposing to form a second polymeric material having an expansion in water at 37° C. after 7 days of less than 1 percent by volume.

13. The composition of claim 12 wherein said liquid further comprises an ethylenically unsaturated organic phosphate ester or phosphonate.

14. The composition of claim 12 wherein said liquid further comprises ethylenically unsaturated organic phosphoric acid ester and said acid ester is from about 20 to about 40 equivalent weight percent neutralized.

15. The composition of claim 12 wherein said first polymeric material has an expansion in water at 37° C. after 90 days of less than 1 percent by volume, and said powder comprises glass having elutable strontium ions.

16. The composition according to claim 12 wherein said second polymeric material has a flexural strength of at least 50 MPa.

17. The composition of claim 12 wherein said liquid further comprising an acid ester is of the general formula:

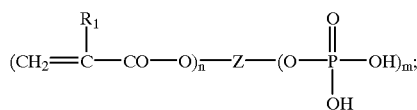

wherein $R_1$ is hydrogen, lower alkyl of from 1 to 5 carbons, halogen or CN radical; n and m are independently integers of 1 or greater, Z is an aliphatic, cycloaliphatic or aryl radical, having a carbon chain comprising at least 2 carbon atoms and 0 or more oxygen or sulfur atoms and having a valency of m+n and containing at least 2 carbon atoms.

18. The composition of claim 12 wherein said liquid further comprises an acid ester mixture of compounds of the general formulas:

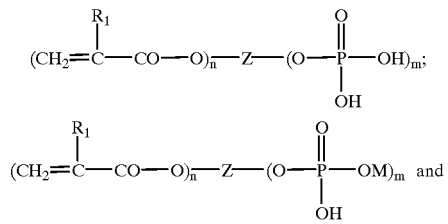

-continued

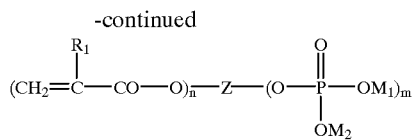

wherein $R_1$ is hydrogen, lower alkyl of from 1 to 5 carbons, halogen or CN radical; n and m are independently integers of 1 or greater, Z is an aliphatic, cycloaliphatic or aryl radical having a carbon chain comprising at least 2 carbon atoms and 0 or more oxygen or sulfur atoms and having a valency of m+n and M, $M_1$ and $M_2$ each is independently a cation.

19. The composition of claim 12 wherein said filler comprises from about 20 to 90 percent by weight of said composition.

20. The composition of claim 12 wherein said photoinitiator is 2,4,6-trimethyl benzoyl phosphine oxide.

* * * * *